United States Patent [19]

Furey et al.

[11] 4,097,104
[45] Jun. 27, 1978

[54] ELECTRICAL CONNECTION SYSTEM

[75] Inventors: Robert J. Furey, Valdosta, Ga.; Lawrence J. Stupay, Endicott, N.Y.

[73] Assignee: Bunker Ramo Corporation, Oak Brook, Ill.

[21] Appl. No.: 711,456

[22] Filed: Aug. 4, 1976

[51] Int. Cl.² .......................................... H01R 13/62
[52] U.S. Cl. ............................ 339/74 R; 128/2.06 E; 128/416
[58] Field of Search ................ 339/17 F, 20, 21, 23, 339/24, 176 MF, 74 R, 97 R, 97 P; 128/2.06 E, 2.1 E, 404, 416, 417, 418, DIG. 4

[56] References Cited

U.S. PATENT DOCUMENTS

| | | | |
|---|---|---|---|
| 2,895,479 | 7/1959 | Lloyd | 128/417 |
| 3,085,577 | 4/1963 | Berman | 128/416 |
| 3,602,216 | 8/1971 | Moe | 128/2.06 E |
| 3,606,881 | 9/1971 | Woodson | 128/2.06 E |
| 3,792,413 | 2/1976 | Hyrlainen | 339/21 R |
| 3,805,159 | 4/1974 | Richelmann | 339/74 R |
| 3,840,840 | 10/1974 | Worth | 339/17 F |
| 4,029,381 | 6/1977 | Tarrall | 339/61 R |
| 4,030,796 | 6/1977 | Patzer | 339/61 R |

*Primary Examiner*—Roy Lake
*Assistant Examiner*—E. F. Desmond
*Attorney, Agent, or Firm*—Hill, Gross, Simpson, Van Santen, Steadman, Chiara & Simpson

[57] ABSTRACT

An electrical connection system is disclosed for connecting two cable conductors to a thin metal plate. The system includes a contact member on the metal plate and a cable connector connected to the dual conductor cable. The contact member has a tunnel section with contact pillars retained therein. The contact pillars have staple-like attachment arms which extend outwardly from the tunnel section, through the metal plate, and are bent back against the metal plate to secure the contact member in place and in electrical contact with the plate. A cable connector having electrical contact members is received and positively supported within the tunnel portion of the contact member. The contact members of the connector engage the contact pillars to complete the connection.

14 Claims, 7 Drawing Figures

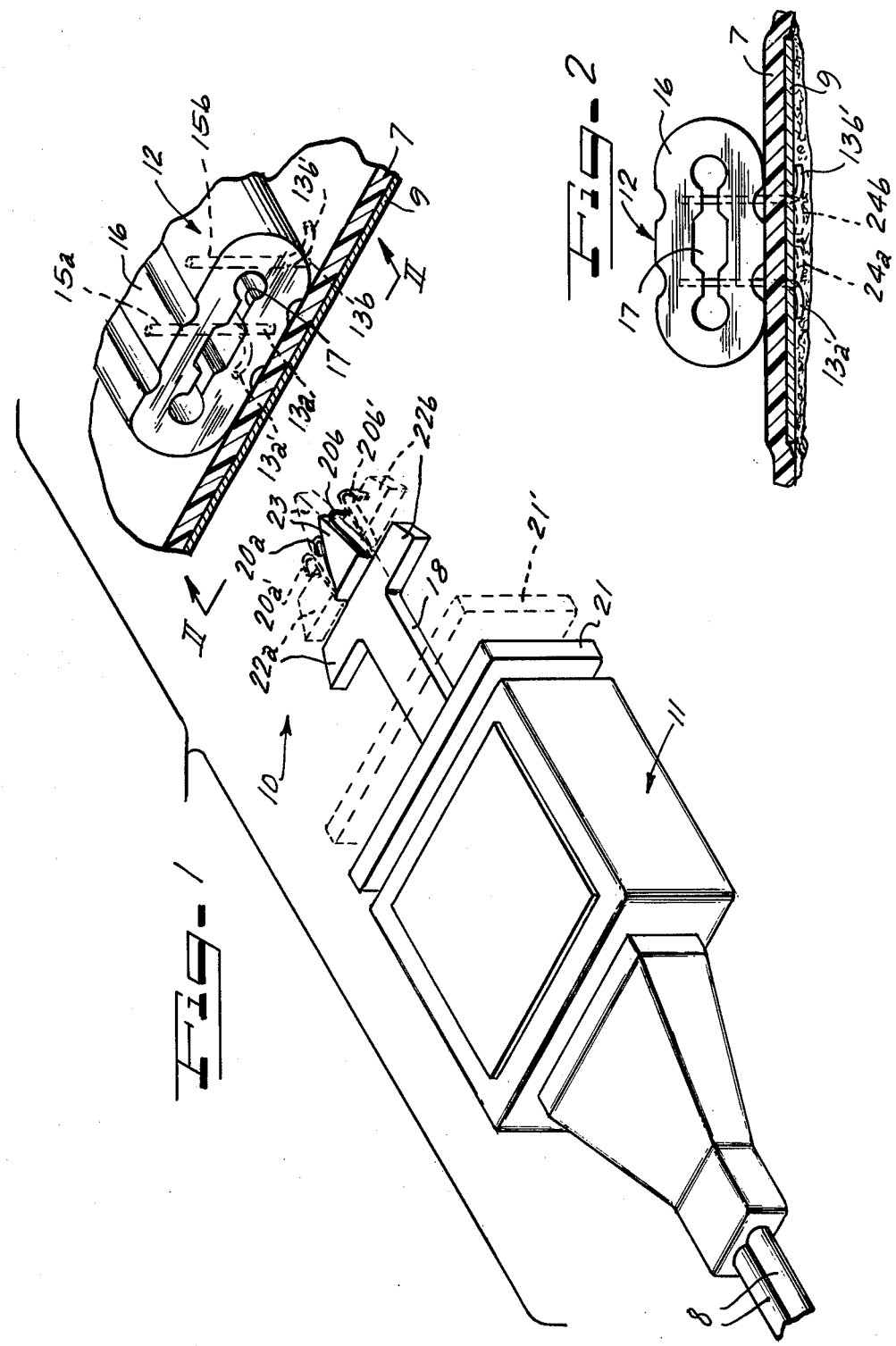

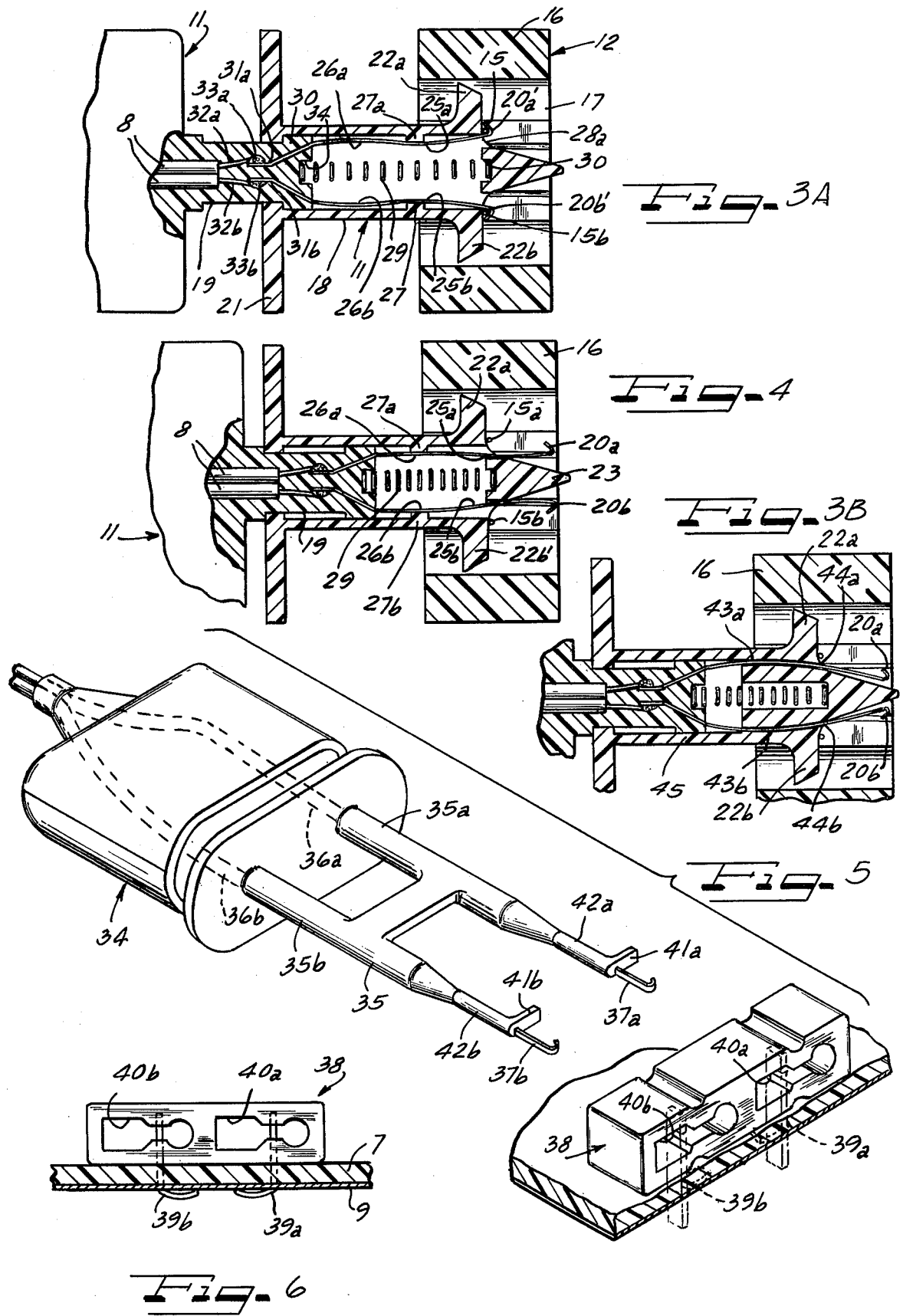

ELECTRICAL CONNECTION SYSTEM

BACKGROUND OF THE INVENTION

1. Field of the Invention

This invention relates to electrical connection systems and more particularly to a connection system for connecting a cable to a thin metal contact plate in electrical connection with a patient.

2. Brief Description of the Prior Art

In the medical electronics industry, it is known to secure a metal contact plate or foil onto a portion of a patient's body by use of a foam pad having an adhesive surface to which the metal foil or plate adheres and which adheres to the patient's body. In order to connect the metal plate or foil to a cable connected to medical electronics instrumentation it is necessary that a connection system be provided between the foil or plate and the cable. Previously, a clothing-type fastening button was utilized as a detachable connection. However, such a connection is undesirable since the fastener may unsnap when slight pressures are placed on the cable near the pad, and since only a single connecting contact is provided.

In U.S. Pat. No. 3,606,881 to Woodson a skin-contacting electrode is described having a terminal which is mounted on the electrode and extends therefrom to provide a connection point for external electrical apparatus. This patent further discloses the use of a terminal 24 connected to the electrode having an enlarged head 34. A cable connecting clip 36 attaches to the terminal 24 to make the electrical connection. This system, however, allows for the connection of only a single conductor to the foil. In medical electronics installations, it is desirable to have contact redundancy by using a two-conductor cable which attaches at two distinctly different points to the foil to guard against intermittent electrical contact. Also, it may be desirable to connect two conductors of the cable to two separate adjacent metal plates or foils. The two contacts may also be used as a fuse type connection for electrical equipment used in surgery.

SUMMARY OF THE INVENTION

It is an object of this invention to provide a connection system to connect multiple cable conductors to a metal plate.

It is a further object of this invention to provide an electrical connection system which is mechanically secure and not subject to intermittent contact or accidental disconnections.

According to the invention, a contact member having a tunnel section with contact pillars retained therein is connected to the thin metal plate. The tunnel section has an oblong-shaped tunnel through which the contact pillars pass. The contact pillars each have a staple-like attachment arm which extends below the tunnel section and through the metal plate. These staple-like attachment arms are bent back against the metal plate to securely mount the contact member. A cable connector is received within the tunnel for both mechanical support and electrical connection to the contact pillars. In one embodiment the cable connector comprises a pair of contact hooks which engage the pillars and are locked in place by a spring loaded telescoping member on the cable connector. The telescoping member has an abutment portion which abuts against an end of the contact hooks to confine the contact pillar within the hook portion.

BRIEF DESCRIPTION OF THE DRAWINGS

FIG. 1 is a perspective view of an electrical connection system according to the invention;

FIG. 2 is a front view of a contact member connected to a thin metal plate for the connection system of this invention;

FIG. 3a is a cut-away plan view of a cable connector for the connection system of this invention;

FIG. 3b is an alternate embodiment for the cable connector of this invention;

FIG. 4 is a plan view of the contact member and cable connector of this invention with the cable connector in a retracted position;

FIG. 5 is a perspective view of an alternate embodiment of the electrical connection system of this invention; and FIG. 6 is a front view of a contact member for the alternate embodiment of FIG. 5.

DESCRIPTION OF THE PREFERRED EMBODIMENTS

As shown in FIG. 1, an electrical connection system according to the teachings of this invention is shown at 10. The principal components of the system are a cable connector 11 connected to a two conductor cable 8, and a contact member 12 in electrical contact with a foil or plate 9 adhered to a foam pad 7.

The contact member 12 has a tunnel section 16 with an oblong-shaped tunnel 17. Within the tunnel section 16 two wire-like contact pillars 15a and 15b are imbedded such that the pillars pass through opposite sides of the tunnel 17. Contact attachment arms 13a and 13b extend below the tunnel section 16 and through the foam pads 7 and foil or plate 9. These attachment arms may then be bent over either inwardly or outwardly in staple-like fashion as shown at 13a' and 13b' or 24a and 24b in FIG. 2.

As shown in FIG. 1, the cable connector 11 has a shaft 19 (shown in FIG. 3a) over which a spring loaded telescoping member 18 is positioned. Contact hooks 20a and 20b extend from the end of the spring loaded telescoping member 18. A retraction lever 21 on the telescoping member 18 allows the member to be drawn back to a retracted position such that the contact hooks are in the position shown at 20a and 20b. In a resting position 21' of the retraction 21 the contact hooks move to a lateral clamped position 20a' and 20b'. In this position, engagement arms 22a and 22b on the telescoping member 18 abut against the contact hooks 20a' to permit locking of contact pillars 15a and 15b thereto. A support tongue 23 on the telescoping member 18 permits the connector 11 to align with and be mechanically supported by a contact member 12. When the connector 11 is in a connected position, this tongue 23 is engaged within a central portion of the tunnel 17 between the pillars 15a and 15b.

An exemplary detailed mechanism for engagement of the contact hooks 20a' and 20b' is shown in FIG. 3a. An inwardly curved portion 25a or 25b is provided on each of the hook arms together with an outwardly curved portion 26a and 26b. A cam or ridge 27a or 27b on the interior of the telescoping member 18 rides along the inwardly and outwardly curved portions of the contact hooks to laterally move the hooks within apertures 28a and 28b at the end of the telescoping member 18. A spring 29 centered within the shaft 19 and retained in position at one end by a seat 34 on the shaft 19 biases the telescoping member 18 outwardly by acting against a seat 30 on the telescoping member 18. Lower ends 31a and 31b of the contact hooks connect with two conductors 32a and 32b within the cable 8 by soldering or crimping techniques at 33a and 33b.

An alternate embodiment for the cable connector 11 is shown in FIG. 3b in which channels 43a and 43b are provided in the end of the telescoping member 18. Within these channels, curved portions 44a and 44b of the contact hooks 20a and 20b are guided such that when a telescoping member 45 is retracted, the curved surface guides the ends of the contact hooks 20a and 20b laterally inwardly toward each other and out of the path of the pillars 15a, 15b. When the member 45 is forward (or member 11 is rearward, to the left in FIG. 5) the hooks 20a, 20b are preferably resiliently urged laterally outwardly snugly against pillars 15a, 15b, at the same time trapping pillars 15a, 15b against the abutments 22a, 22b.

FIGS. 5 and 6 illustrate an alternate embodiment for the connection system of this invention in which a cable connector 34 has a spring-loaded H-shaped telescoping member 35. Dual shafts 36a and 36b as shown in dotted lines have contact hooks 37a and 37b connected thereto. The H-shaped telescoping member 35 has telescoping portions 35a and 35b aligned over the shafts 36a and 36b. Abutment surfaces 41a and 41b are also provided at ends of the H-shaped member against which tips of the hooks 37a and 37b are drawn. With this embodiment, a contact member 38 is provided having dual tunnels 40a and 40b. To make contact, member 35 is retracted and contact hooks 37a and 37b are manually positioned to grab the pillars 39a and 39b. The telescoping member 35 is then released and the abutment surfaces 41a and 41b lock the contact hooks to the pillars 39a and 39b and maintain the parts in fixed supported position.

It may be observed that in the embodiments shown, the pillars are spaced apart and are electrically connected to each other only via the thin conductive plate. In this arrangement, accordingly, the cables 8 may be connected respectively to surgical equipment and a ground whereby the thin plate 9 may act as an element of the circuit. Alternatively, the pillars 15a, 15b may be integrally connected at the top of the tunnel, as viewed in FIG. 2, in which case the pillars provide parallel electrical paths to the foil, whether or not the cables 8 are otherwise electrically interconnected.

Although various minor modifications may be suggested by those versed in the art, it should be understood that we wish to embody within the scope of the patent hereon, all such embodiments as reasonably come within the scope of our contribution to the art.

We claim as our invention:

1. An electrical connection system for connecting to a thin metal plate, comprising: a contact member having a tunnel section with electrically conductive contact pillars retaining within the tunnel section, extensions of said contact pillars forming staple-like attachment arms extending outwardly from said tunnel section; and a thin metal plate upon which said contact member is mounted, said staple-like attachment arms extending through said metal plate and being deformed against said metal plate to draw said contact member against the thin metal plate.

2. The connection system of claim 1 in which the contact member tunnel section is an insulator and has a tunnel with an oblong-shape, said contact pillars being spaced transverse to the axis of said tunnel, and exposed within said tunnel.

3. The connection system of claim 1 in which the thin metal plate has a foam pad thereover with an adhesive means for retaining the thin metal plate and also for fixing the thin metal plate on a medical patient, said form pad being positioned between said thin metal plate and contact member tunnel section.

4. The connection system of claim 1 in which said tunnel section has a tunnel means with a longitudinal axis parallel to the surface of said metal plate for receiving a cable connector for connection to said contact pillars, said tunnel means also providing mechanical stability for said cable connector.

5. An electrical connection system for connecting cable conductors to a thin metal plate, comprising: a contact member having a tunnel section with contact pillars retained within the tunnel section, extensions of said contact pillars forming staple-like attachment arms extending outwardly from said tunnel section for passage through and engaging the metal plate by stapling; and a cable connector received in said contact member tunnel section having conductive connection means for connecting the cable conductors to said contact pillars.

6. The connection system of claim 5 wherein said conductive connection means include spaced conductors and means resiliently urging said conductors against said pillars in positive retained position thereagainst.

7. The connection system of claim 5 in which the cable connector includes support means adjacent the connection means, said support means being received against said tunnel section and mechanically positively positioning the connector therein.

8. An electrical connection system for connecting cable conductors to a metal plate, comprising: a thin metal plate; a contact member connected to said thin metal plate having a tunnel section with contact pillars retained within the tunnel section and passing through and exposed in a tunnel portion thereof, said contact pillars having staple-like attachment arms extending outwardly from said tunnel section, through said metal plate, and being deformed against said metal plate; and a cable connector received in said contact member tunnel section and having conductive connection means for connecting the cable conductors to said contact pillars.

9. An electrical connection system, comprising: spaced, conductive contact pillrs retained in a tunnel section and passing through side walls of a tunnel in the tunnel section, said contact pillars being mechanically and electrically connected to a foil electrode; a multiple conductor cable; and a cable connector having connection means for connecting the cable conductors to the contact pillars by releasable positively positioned abutting contacts.

10. The system of claim 9 in which said cable connector connection means comprises dual shafts, each having a contact hook connected thereto and a telescoping spring loaded member over said shaft, said contact hook protruding from an end of said telescoping member.

11. The system of claim 9 in which the cable connector connection means comprises a shaft, two contact hooks on opposite sides of said shaft, and a spring-loaded telescoping member over said shaft, said contact hooks protruding through an end of said telescoping member, said telescoping member providing an abutment surface for said contact hooks and said pillars.

12. The system of claim 11 in which said connection means includes means for laterally deflecting said contact hooks away from said pillars when the telescoping member is retracted.

13. The system of claim 12 in which said means for laterally deflecting comprises abutments on said telescoping member and a curved portion on said contact hooks.

14. The system of claim 12 in which said means for laterally deflecting comprises curved channels in said telescoping member and a curved portion on said contact hooks.

* * * * *